US009277909B2

(12) United States Patent
Brunsvold

(10) Patent No.: US 9,277,909 B2
(45) Date of Patent: Mar. 8, 2016

(54) SUTURE ANCHOR

(75) Inventor: Mark D. Brunsvold, Sturgeon Bay, WI (US)

(73) Assignee: Parcus Medical, LLC, Sarasota, FL (US)

( * ) Notice: Subject to any disclaimer, the term of this patent is extended or adjusted under 35 U.S.C. 154(b) by 798 days.

(21) Appl. No.: 12/290,226

(22) Filed: Oct. 27, 2008

(65) Prior Publication Data
US 2009/0149883 A1 Jun. 11, 2009

Related U.S. Application Data

(60) Provisional application No. 60/983,159, filed on Oct. 27, 2007, provisional application No. 61/127,315, filed on May 12, 2008.

(51) Int. Cl.
*A61B 17/04* (2006.01)

(52) U.S. Cl.
CPC ..... *A61B 17/0401* (2013.01); *A61B 2017/0414* (2013.01); *A61B 2017/0441* (2013.01)

(58) Field of Classification Search
CPC ............... A61B 2017/0414; A61B 2017/0441; A61B 17/0401
USPC ......... 606/222, 223, 224, 225, 226, 227, 301, 606/72, 73, 75, 104, 139, 144, 232, 300, 606/304
See application file for complete search history.

(56) References Cited

U.S. PATENT DOCUMENTS

| 5,217,486 A | 6/1993 | Rice et al. |
| 5,269,809 A | 12/1993 | Hayhurst et al. |
| 5,480,403 A * | 1/1996 | Lee et al. ...................... 606/232 |
| 5,569,306 A | 10/1996 | Thal |
| 5,593,410 A | 1/1997 | Vrespa |
| 5,658,313 A | 8/1997 | Thal |
| 5,665,112 A | 9/1997 | Thal |
| 5,683,419 A | 11/1997 | Thal |
| 5,899,921 A | 5/1999 | Caspari et al. |
| 5,902,321 A | 5/1999 | Caspari et al. |
| 5,906,632 A | 5/1999 | Bolton |
| 5,935,129 A | 8/1999 | McDevitt et al. |
| 5,957,953 A | 9/1999 | Dipoto et al. |
| 5,964,768 A | 10/1999 | Huebner |
| 6,027,523 A | 2/2000 | Schmieding |
| 6,508,830 B2 | 1/2003 | Steiner |

(Continued)

FOREIGN PATENT DOCUMENTS

| WO | WO 97/30649 A1 | 8/1997 |
| WO | WO-00/44293 | 8/2000 |

(Continued)

*Primary Examiner* — Gregory Anderson
*Assistant Examiner* — Christina Lauer
(74) *Attorney, Agent, or Firm* — Bergman & Song LLP; Michael Bergman

(57) ABSTRACT

An anchor device and system for coupling soft tissue to osseous tissue includes a stopper member that supports a loop of suture material. A fixing member includes features that allow it to be rigidly coupled to surrounding bone and thus hold the stopper member in a cavity within the bone. The loop of suture material, in turn, supports a second suture device, which is coupled to, and thus retains, the soft tissue. In certain embodiments, the stopper member includes a mechanical linkage for coupling it to the fixing member, and surface features that resist withdrawal of the fixing member from the bone.

8 Claims, 24 Drawing Sheets

(56) References Cited

U.S. PATENT DOCUMENTS

| | | | |
|---|---|---|---|
| 6,527,794 B1 | 3/2003 | McDevitt et al. | |
| 6,575,976 B2 | 6/2003 | Grafton | |
| 6,585,730 B1 | 7/2003 | Foerster | |
| 6,641,596 B1 | 11/2003 | Lizardi | |
| 6,652,563 B2 | 11/2003 | Dreyfuss | |
| 6,692,516 B2 | 2/2004 | West, Jr. et al. | |
| 6,840,953 B2 * | 1/2005 | Martinek | 606/232 |
| 6,855,157 B2 | 2/2005 | Foerster et al. | |
| 6,923,824 B2 * | 8/2005 | Morgan et al. | 606/232 |
| 6,984,241 B2 | 1/2006 | Lubbers et al. | |
| 7,081,126 B2 | 7/2006 | McDevitt et al. | |
| 7,226,469 B2 | 6/2007 | Benavitz et al. | |
| 7,381,213 B2 | 6/2008 | Lizardi | |
| 2001/0021862 A1 | 9/2001 | Bonutti et al. | |
| 2001/0025181 A1 | 9/2001 | Freedlan | |
| 2002/0052629 A1 | 5/2002 | Morgan et al. | |
| 2002/0052630 A1 | 5/2002 | Morgan et al. | |
| 2002/0077631 A1 | 6/2002 | Lubbers et al. | |
| 2002/0095180 A1 | 7/2002 | West, Jr. et al. | |
| 2003/0060887 A1 | 3/2003 | Ek | |
| 2003/0130695 A1 | 7/2003 | McDevitt et al. | |
| 2003/0149448 A1 | 8/2003 | Foerster et al. | |
| 2003/0195563 A1 | 10/2003 | Foerster | |
| 2003/0225456 A1 | 12/2003 | Ek | |
| 2004/0002735 A1 | 1/2004 | Lizardi et al. | |
| 2004/0093031 A1 | 5/2004 | Burkhart et al. | |
| 2004/0098052 A1 | 5/2004 | West, Jr. et al. | |
| 2004/0193167 A1 | 9/2004 | Tucciarone et al. | |
| 2005/0033363 A1 | 2/2005 | Bojarski et al. | |
| 2005/0055052 A1 | 3/2005 | Lombardo et al. | |
| 2005/0075668 A1 | 4/2005 | Lizardi | |
| 2005/0149122 A1 | 7/2005 | McDevitt et al. | |
| 2005/0234460 A1 | 10/2005 | Miller | |
| 2005/0240199 A1 | 10/2005 | Martinek et al. | |
| 2005/0240226 A1 | 10/2005 | Foerster et al. | |
| 2005/0245932 A1 | 11/2005 | Fanton et al. | |
| 2005/0267479 A1 | 12/2005 | Morgan et al. | |
| 2006/0079904 A1 | 4/2006 | Thal | |
| 2006/0106423 A1 | 5/2006 | Weisel et al. | |
| 2006/0201519 A1 | 9/2006 | Frazier et al. | |
| 2006/0207606 A1 | 9/2006 | Roue et al. | |
| 2006/0207608 A1 | 9/2006 | Hirotsuka et al. | |
| 2006/0207612 A1 | 9/2006 | Jackson et al. | |
| 2006/0259076 A1 | 11/2006 | Burkhart et al. | |
| 2006/0271060 A1 | 11/2006 | Gordon | |
| 2006/0282081 A1 | 12/2006 | Fanton et al. | |
| 2006/0282083 A1 | 12/2006 | Fanton et al. | |
| 2007/0049944 A1 | 3/2007 | Stone et al. | |
| 2007/0073299 A1 | 3/2007 | Dreyfuss et al. | |
| 2007/0135841 A1 | 6/2007 | Dreyfuss | |
| 2007/0142835 A1 | 6/2007 | Green et al. | |
| 2007/0156148 A1 | 7/2007 | Fanton et al. | |
| 2007/0156149 A1 | 7/2007 | Fanton et al. | |
| 2007/0156150 A1 | 7/2007 | Fanton et al. | |
| 2007/0156176 A1 | 7/2007 | Fanton et al. | |
| 2007/0203498 A1 | 8/2007 | Gerber et al. | |
| 2007/0219557 A1 | 9/2007 | Bourque et al. | |
| 2007/0219558 A1 | 9/2007 | Deutsch | |
| 2007/0225719 A1 * | 9/2007 | Stone et al. | 606/72 |
| 2007/0255317 A1 | 11/2007 | Fanton et al. | |
| 2007/0260259 A1 | 11/2007 | Fanton et al. | |
| 2008/0004659 A1 | 1/2008 | Burkhart et al. | |
| 2008/0009904 A1 | 1/2008 | Bourque et al. | |
| 2008/0015540 A1 | 1/2008 | Muni et al. | |
| 2008/0023012 A1 | 1/2008 | Dineen et al. | |
| 2008/0027560 A1 | 1/2008 | Jackson et al. | |
| 2008/0033460 A1 | 2/2008 | Ziniti et al. | |
| 2008/0035160 A1 | 2/2008 | Woodson et al. | |
| 2008/0051836 A1 | 2/2008 | Foerster et al. | |
| 2008/0058584 A1 | 3/2008 | Hirotsuka et al. | |
| 2008/0086138 A1 | 4/2008 | Stone et al. | |
| 2008/0103528 A1 | 5/2008 | Zirps et al. | |
| 2008/0109038 A1 | 5/2008 | Steiner et al. | |
| 2008/0161864 A1 | 7/2008 | Beck et al. | |
| 2008/0208265 A1 | 8/2008 | Frazier et al. | |
| 2008/0215091 A1 | 9/2008 | Dreyfuss | |
| 2008/0249567 A1 | 10/2008 | Kaplan | |

FOREIGN PATENT DOCUMENTS

| | | |
|---|---|---|
| WO | WO 2006/099109 A2 | 9/2006 |
| WO | WO-2008/097403 | 8/2008 |

* cited by examiner

SUTURE ANCHOR

CROSS-REFERENCE TO RELATED APPLICATIONS

The present application claims the benefit of U.S. provisional patent applications numbered 60/983,159 filed on 27 Oct, 2007 and 61/127,315 filed on 12 May, 2008, the disclosures of which are herewith incorporated by reference in their entirety.

FIELD OF THE INVENTION

The present invention relates to surgical devices and more particularly to devices for surgical attachment.

BACKGROUND

Various surgical procedures require the temporary or permanent coupling of tissue to hard tissue such as bone. For example, when a tendon or ligament becomes detached from the bone which normally supports it, reattachment of the soft tissue to the bone with a supporting device helps to position the soft tissue for regrowth and recovery. Under other circumstances it is desirable to have a secure means of attaching a length of suture material between one or more bony regions. With this in mind, a variety of approaches have been developed for securing suture to hard tissue such as bone. Classed generally as bone anchors, these approaches have met with varying success.

Certain devices among those in this class have provided limited coupling strength with respect to a surrounding bone substrate matrix. Other devices have provided limited coupling strength and durability with respect to a suture material. Others have provided inadequate positional adjustability of the suture material. These and other deficiencies persist despite long and well-funded efforts by many investigators to secure improved methods and devices.

SUMMARY

Being aware of the long and previously incompletely effective efforts of others to address these problems, the present inventor has arrived at a new and important understanding of the problems, and of the mechanisms underlying those problems. Having developed this knowledge through careful and diligent effort, the inventor has now conceived and, out of similarly diligent efforts, reduced to practice novel and effective solutions to these problems. In particular, it is understood that earlier efforts to anchor soft tissue to bone have been inconsistently effective. The inventor now presents new and effective methods, devices and systems to effect these and other purposes.

As discussed above, it is necessary in some surgical procedures to provide a mechanism for coupling soft tissue to a particular location within the body. For example, in some circumstances it is necessary to couple a ligament or tendon to a bone. In other circumstances soft tissue such as muscle or skin must be similarly fixed in place.

One method of achieving such a coupling is to embed at least a portion of an anchor within a bone, and couple a suture between the anchor and the soft tissue. To this end, the present invention includes methods, systems and apparatus for providing an anchor device including a suture for coupling between, for example, bone and soft tissue.

In one embodiment, the anchor device includes a stopper portion and a fixing portion. The stopper portion is adapted to be coupled to a loop of suture material. A further length of suture material is disposed in a bent configuration through the suture loop. The stopper portion is disposed within a substrate matrix of osseous tissue and held in place by the fixing portion.

In certain embodiments according to the invention, the fixing portion includes a threaded feature on an external surface thereof. In other embodiments according to the invention a fixing portion includes a barbed feature on an external surface thereof. In still other embodiments according to the invention a fixing portion includes a vaned feature on an external surface thereof.

In certain embodiments of the invention, the fixing portion includes a plurality of projecting features disposed between longitudinal grooves at an external surface of the fixing portion. In other embodiments of the invention, the fixing portion includes a plurality of barb projections where the barb projections include substantially circular barb projections disposed coaxially about a longitudinal axis of the fixing portion. In other embodiments, the barb projections include a plurality of projections disposed between longitudinal grooves at a surface of the fixing portion.

In certain embodiments of the invention, the stopper portion is disposed between two or more fixing portions. In certain embodiments of the invention, fixing portions are provided with opposite threads and a coupling mechanism. In still further embodiments of the invention, the stopper portion includes a threaded surface feature oppositely handed with respect to a threaded surface feature of a fixing portion. In certain embodiments, the stopper portion includes a detent mechanism adapted to couple the stopper portion in substantially fixed spatial relationship with respect to the fixing portion.

These and other advantages and features of the invention will be more readily understood in relation to the following detailed description of the invention, which is provided in conjunction with the accompanying drawings.

DETAILED DESCRIPTION

Figure 1:
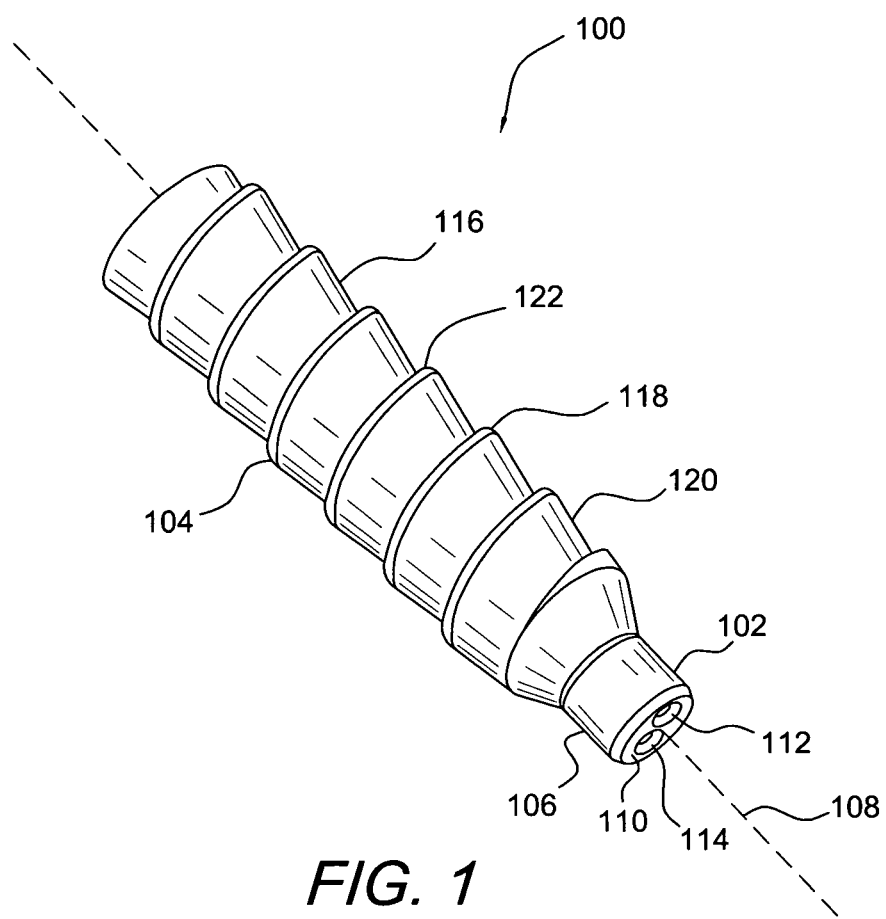
FIG. 1 shows, in perspective side view, an exemplary anchor device including a stopper portion and a fixing portion according to one embodiment of the invention.

FIG. 1 shows part of an exemplary anchor 100 according to one embodiment of the invention. The anchor 100 includes a first stopper portion 102 and a second fixing portion 104. The stopper portion 102 has a substantially circular cylindrical peripheral surface 106 disposed coaxially about a longitudinal axis 108. A distal surface 110 of the stopper 102 is disposed substantially normal to the longitudinal axis 108. In the illustrated embodiment, first and second bores are defined within the stopper 102. Each bore is defined by a respective substantially cylindrical internal surface 112, 114. Internal surfaces 112, 114 have respective longitudinal axes disposed substantially parallel to one another and to longitudinal axis 108.

In the illustrated embodiment, fixing portion 104 of the anchor 102 is generally cylindrical about longitudinal axis 108. A circumferential surface 116 of fixing portion 104 includes a plurality of detent formations. As illustrated, the detent formations include a substantially helical flange 118 or ridge disposed generally equidistant to longitudinal axis 108. As illustrated, the helical flange 118 includes a first distal surface region 120 and a second proximal surface region 122. As illustrated in FIG. 1, the detent formation is shown as a push-in style detent feature. One of skill in the art will appreciate, however, that other detent features, such as, for example, cortical bone threads and cancellous bone threads are to be used in other respective embodiments of the invention. Also, as shown, the push-in detent features extend over the full length of the fixing portion 104, as shown. In other embodiments partial coverage is employed.

As will be discussed in additional detail below, the fixing portion 104 includes an internal surface defining a bore that is substantially coaxial with longitudinal axis 108. In the configuration illustrated, where the stopper portion 102 is disposed adjacent to a proximal end of the fixing portion 104 open regions within bores 112 and 114 are contiguous with an open region within the longitudinal bore of the fixing portion 104.

According to one embodiment of the invention, the stopper portion 102 is removably coupled to the fixing portion 104 in the illustrated orientation. According to one methodical aspect of the invention stopper portion 102 is removably coupled to fixing portion 104 prior to insertion of the resulting assembly into osseous tissue. In an alternative it embodiment of the invention stopper portion 102 is disposed within a region of osseous tissue and fixing portion 104 is subsequently disposed adjacent to stopper portion 102. In a further embodiment, stopper portion 102 is substantially non-removal.

In one embodiment of the invention, the helical flange 118 is configured as a thread, whereby a method of rotating fixing portion 104 about longitudinal axis 108 causes a threading interaction between helical flange 118 and a surrounding bone tissue. Consequently the rotation of the fixing portion 104 causes a distal advancement of the fixing portion 104 into the bone tissue.

As will be described below in further detail, a method according to one embodiment of the invention includes disposing respective first and second portions of a length of suture substantially coaxially within bores 112 and 114. The length of suture includes a further U-shaped portion disposed within the bore of the fixing portion 104 and contiguous with the first and second suture portions. According to one embodiment of the invention, first and second knots are formed at respective ends of the length of suture and are disposed distally of surface 108 so as to slidingly couple the length of suture to the stopper portion 106.

Figure 2:
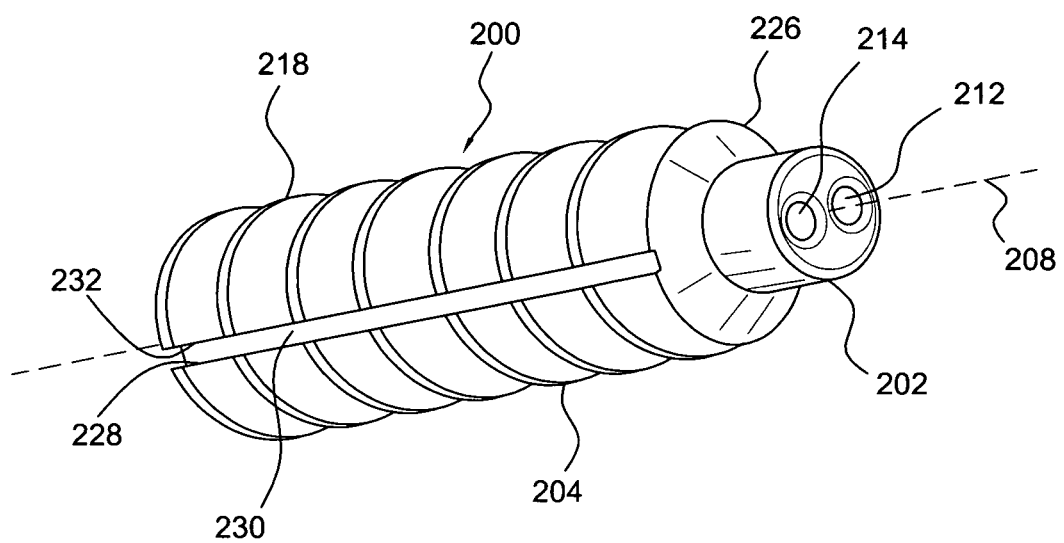
FIG. 2 shows, in perspective side view, an exemplary anchor device including a fixing device having a longitudinal groove according to one embodiment of the invention.

FIG. 2 shows an oblique generally distal perspective view of a portion of an anchor 200 according to one embodiment of the invention. Like anchor 100, anchor 200 includes a stopper portion 202 and a fixing portion 204. The stopper portion 202 includes first and second generally longitudinal bores 212 and 214. In the embodiment shown, the longitudinal bores 212 and 214 are defined by respective substantially cylindrical internal surfaces of the stopper portion 202. According to one embodiment of the invention, these substantially cylindrical internal surfaces are substantially smooth and uninterrupted. The stopper portion 202 is adapted to be disposed adjacent to, and in some embodiments coupled to, a distal end 226 of fixing portion 204.

The fixing portion 204 includes a generally cylindrical external surface 216 having a helical flange 218 formation. A groove 228 is disposed longitudinally along surface 216 and defines respective first and second ends of flange 218. In the illustrated embodiment, flange 218 is generally helical. Consequently, flange end 230 is distally offset along a longitudinal axis 208 with respect to flange end 232.

In another embodiment of the invention, the flange 218 formation is substantially circular, rather than helical, so that flange ends 230, 232 are disposed generally adjacent to one another across groove 228. It should be noted that in either case, flange 218 does not form an uninterrupted helical thread about longitudinal axis 218. In a further embodiment, fixing portion 204 includes a plurality of longitudinal grooves disposed generally parallel to groove 228 around longitudinal axis 208.

Figure 3:
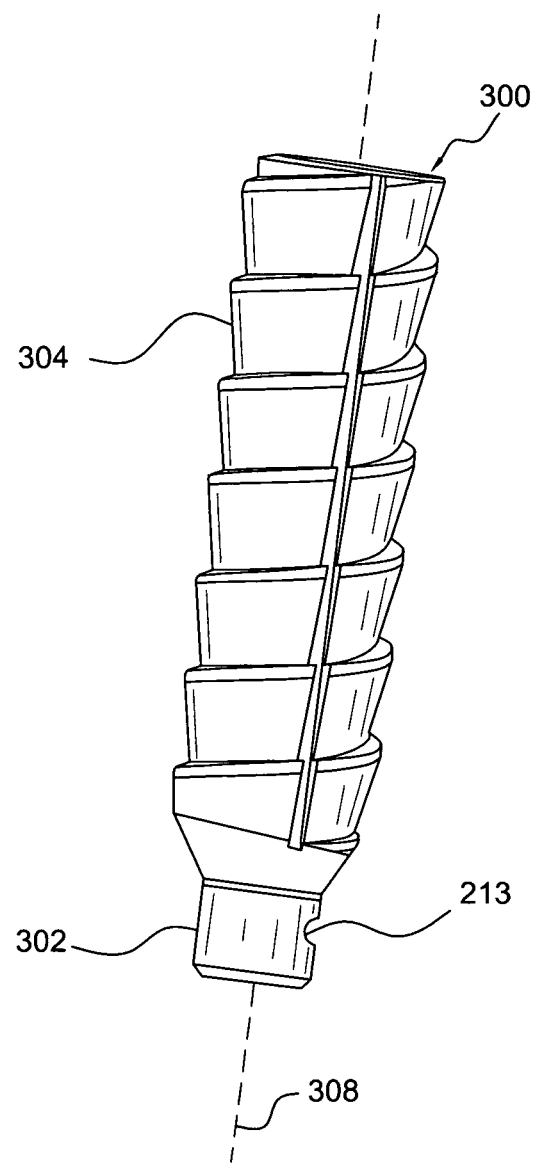
FIG. 3 shows, in perspective side view, an exemplary anchor device including a stopper device having a radial suture loop bore according to one embodiment of the invention.

FIG. 3 shows an anchor 300 including a stopper portion 302 and a fixing portion 304 according to still another embodiment of the invention. While the configuration of anchor 300 is generally similar to that of anchor 200, it should be noted that stopper portion 302 includes a bore 213 disposed generally perpendicular to a longitudinal axis 308. One of skill in the art will appreciate that bore 213 defines an internal right angle within stopper portion 302 so as to open at a distal end of an internal longitudinal bore within the fixing portion 304. Thus a length of suture can be passed through bore 213 to form an internal loop within the longitudinal bore of the fixing portion. An end of the length of suture projects perpendicular to longitudinal axis to emerge through the illustrated orifice where it is knotted to retain the length of suture in sliding relation to the stopper portion. One of skill in the art will appreciate that this arrangement contrasts to the longitudinal bores 212, 214 of anchor 200.

Figure 4:
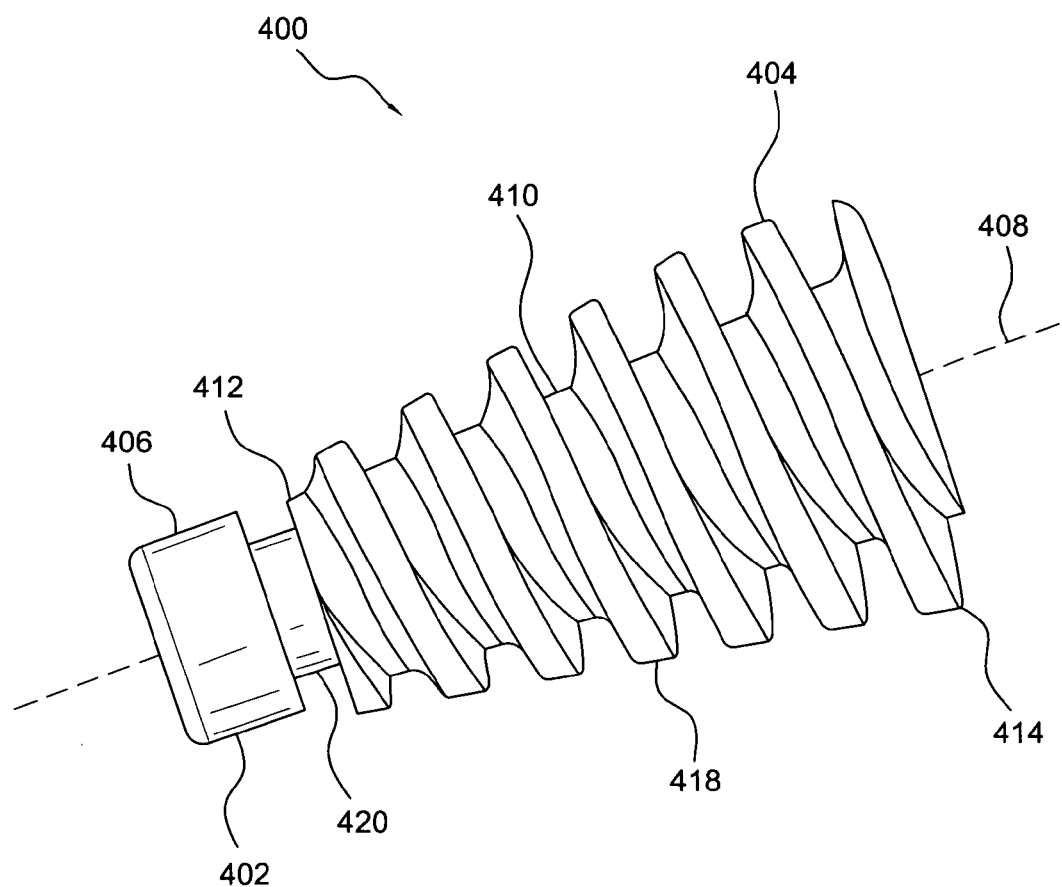
FIG. 4 shows, in perspective side view, an exemplary anchor device including a stopper device having a projection according to one embodiment of the invention.

FIG. 4 shows, in perspective view, a portion of an anchor 400 according to a further embodiment of the invention. The anchor includes a stopper portion 402 and a fixing portion 404. The fixing portion 404 has a generally circular symmetry about a longitudinal axis 408. A circumferential external surface 410 of the fixing portion has a first relatively smaller radius perpendicular to longitudinal axis 408 at a distal end 412 of the fixing portion. In comparison a corresponding radius at a second proximal end 414 of the fixing portion 404 is relatively larger. Consequently, external surface 410 of the fixing portion 404 describes, generally, a frustum of a cone. In the illustrated embodiment, the external surface 410 includes a projecting ridge or flange 418 disposed in a generally spiral/helical configuration about longitudinal axis 408. In various embodiments, the ridge or flange 418 is interrupted by one or more longitudinal grooves like that shown in anchor 300 of FIG. 3. It should be noted that while FIG. 4 exemplifies an anchor having a cortical thread alternative threading and other retaining features are used in alternative embodiments respectively.

In the illustrated embodiment, stopper portion 402 includes a generally circular cylindrical external surface 406 disposed coaxially to axis 408 at a distal region of the stopper. The stopper 402 also has a projecting portion 420 at a proximal region thereof. In various embodiments, as will be described below in additional detail, the projecting portion 420 is adapted to be received within a corresponding cavity of the fixing portion 404. According to one embodiment the corresponding cavity consists of a portion of a longitudinal bore.

Figure 5:
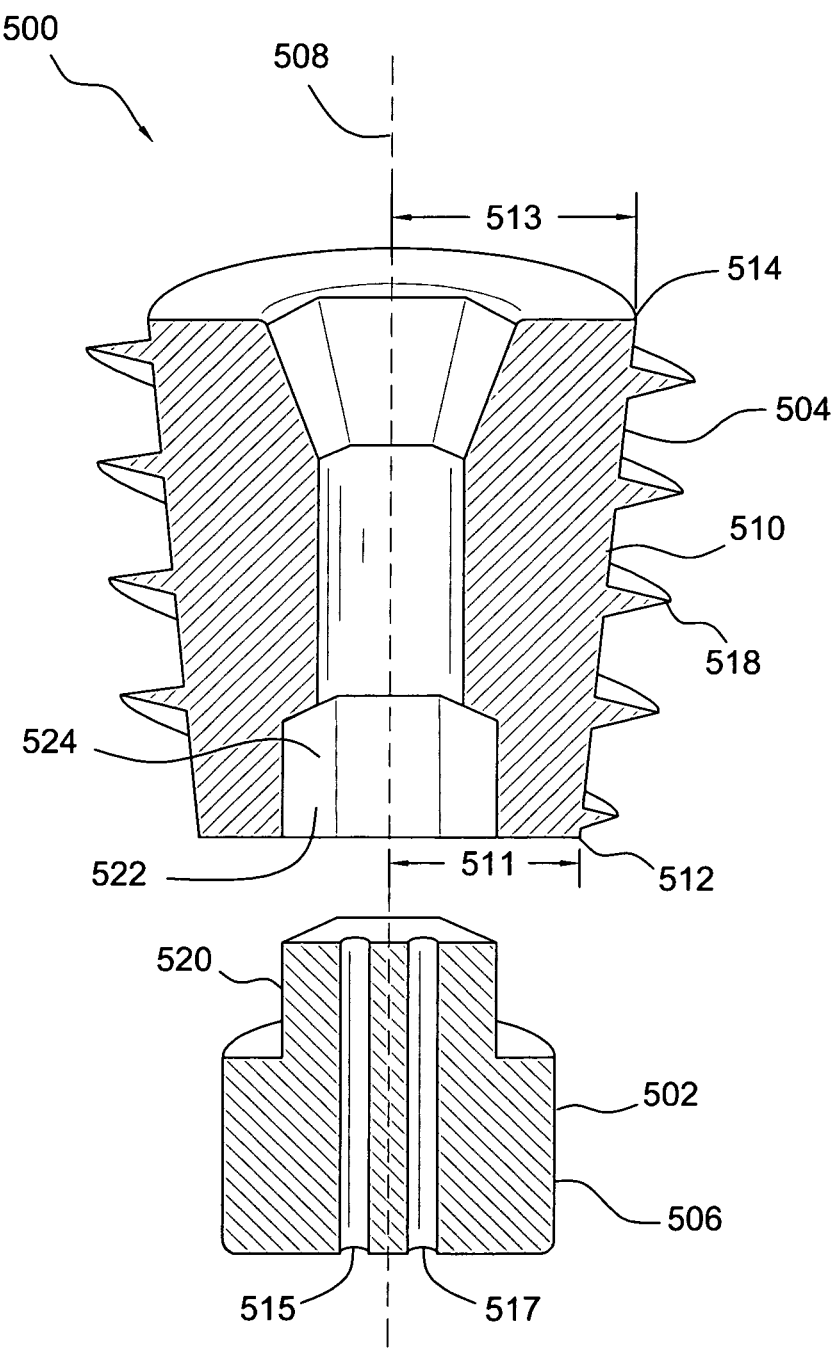
FIG. 5 shows, in cross-section, an anchor according to one embodiment of the invention.
Figure 6A:
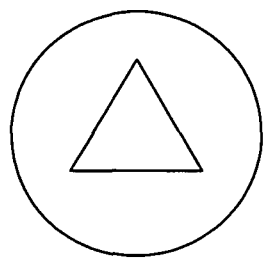
FIGS. 6A-6H show a respective plurality of projection profiles according to respective exemplary embodiments of the invention.
Figure 6B:
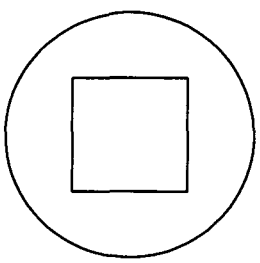
Figure 6C:
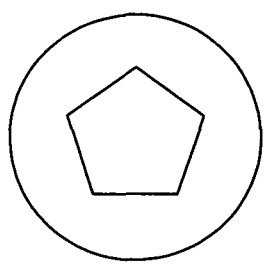
Figure 6D:
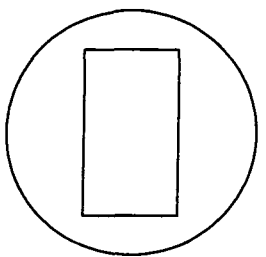
Figure 6E:
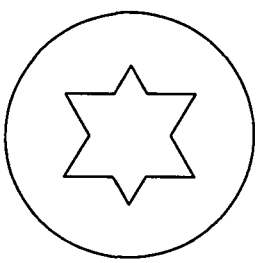
Figure 6F:
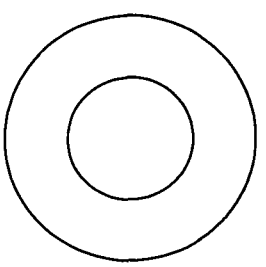
Figure 6G:
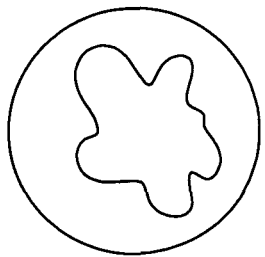
Figure 6H:
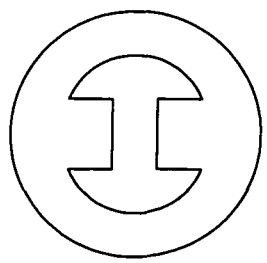

FIG. 5 shows, in cross-section, a portion of an exemplary anchor 500. Anchor 500 includes a stopper portion 502 and a fixing portion 504. The fixing portion 504 has a generally circular symmetry about a longitudinal axis 508. A circumferential external surface 510 of the fixing portion has a first relatively smaller radius 511 perpendicular to longitudinal axis 508 at a distal end 512 of the fixing portion. In comparison a corresponding radius at a second proximal end 514 of the fixing portion 504 is relatively larger. Consequently, external surface 510 of the fixing portion 504 describes, generally, a frustum of a cone.

As shown, longitudinal bores 515, 517 traverse the stopper portion 502. The longitudinal bores are disposed generally parallel to longitudinal axis 508. As will be discussed below in further detail, the longitudinal bores 515, 517 are adapted to receive respective portions of a suture loop.

In the illustrated embodiment, stopper portion 502 includes a generally circular cylindrical external surface 506 disposed coaxial to axis 508 at a distal region of the stopper. The stopper 502 also has a projecting portion 520 at a proximal region thereof. As illustrated, the projecting portion 520 is adapted to be received within a corresponding cavity 522 of the fixing portion 504. As illustrated, cavity 522 is defined by a plurality of substantially planar surface regions, e.g., 524. Consequently, a cross-sectional profile of the cavity 522 is, in certain embodiments, polygonal. A corresponding cross-section of projecting portion 520 matches the polygonal cross-section of the cavity 522, in size and shape, so that the cavity is adapted to receive the projecting portion 520 firmly therewithin.

The creative practitioner of ordinary skill in the art will appreciate that a wide variety of cross-sections are used in corresponding embodiments of the invention. Thus, while the cross-section of projecting portion 520 is shown as generally hexagonal, other useful cross-sections include, as shown in FIG. 6, triangular (FIG. 6A), square (FIG. 6B), pentagonal (FIG. 6C), elongate (FIG. 6D), stellate (FIG. 6E), circular (FIG. 6F), irregular (FIG. 6G) and combinations thereof, (e.g., FIG. 6H).

Figure 7:
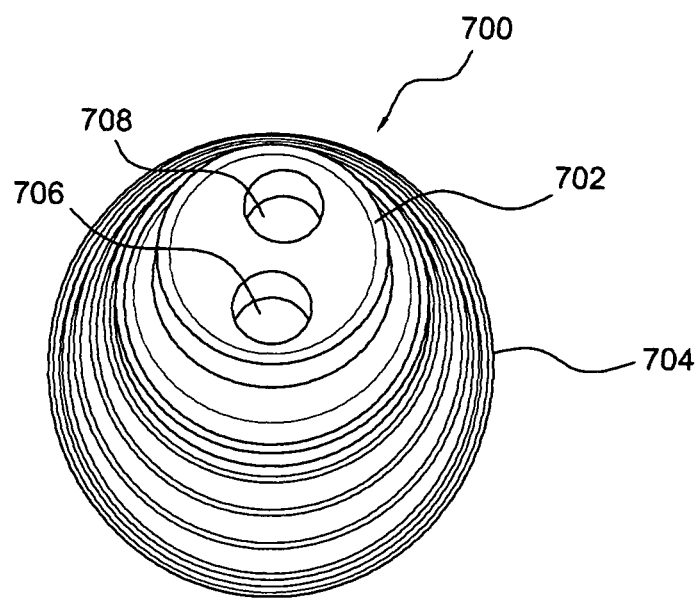
FIG. 7 shows, in distal perspective view, an anchor device according to one embodiment of the invention.

FIG. 7 shows, in distal perspective view, an exemplary anchor 700 including a stopper portion 702 and a fixing portion 704. As is evident on inspection, longitudinal bores 706 and 708 in the stopper portion 702 form a contiguous passage with a longitudinal bore of the fixing portion 704.

Figure 8:
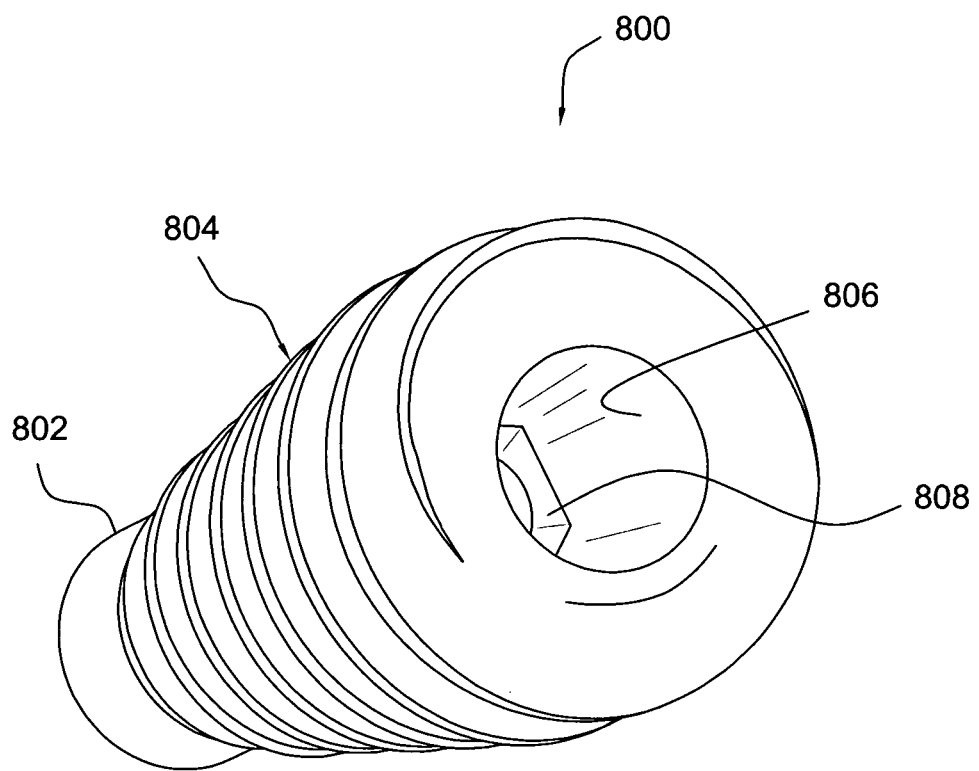
FIG. 8 shows, in proximal perspective view, an anchor device according to one embodiment of the invention.

FIG. 8 shows, in proximal perspective view, an exemplary anchor 800 including a stopper portion 802 and a fixing portion 804. A portion of a longitudinal bore 806 within the fixing portion 804 is visible. As shown, an internal surface of the longitudinal fixing portion 804 includes a plurality of substantially planar surface regions e.g., 808 defining a substantially hexagonal tool engagement region 806.

The substantially hexagonal tool engagement region 806 is adapted to receive a portion of a driving tool of corresponding cross-section therewithin. One of skill in the art will appreciate that such a tool can be used to rotate or otherwise manipulate the fixing portion as part of an anchor insertion procedure and method. It will also be evident to one of skill in the art that, while the illustrated embodiment shows a tool engagement region of the longitudinal bore having a substantially hexagonal cross-section, a wide variety of other cross-sections and configurations can readily be used in various embodiments of the invention.

Figure 9:
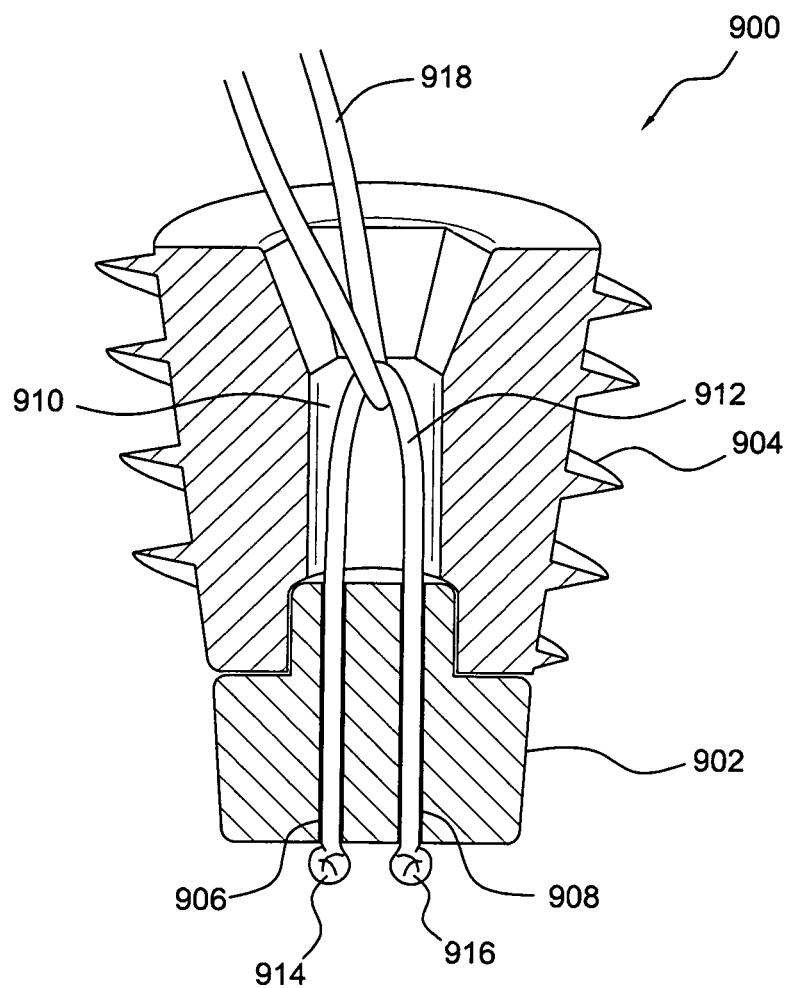
FIG. 9 shows, in cross-section, a suture loop according to one embodiment of the invention.

FIG. 9 shows, in cross-section, a portion of anchor 900 including a suture loop according to one embodiment of the invention. As shown, the anchor includes a stopper portion 902 and a fixing portion 904. The stopper portion 902 includes first 906 and second 908 longitudinal bores that, when the stopper portion 902 is disposed adjacent to the fixing portion 904, open onto a longitudinal bore 910 of the fixing portion 904. A first length of suture 912 is adapted to be knotted 914 at first end, to pass through the first stopper portion bore 906 into the fixing portion bore 910 and back through the second stopper portion bore 908.

A further knot 916 is adapted to retain the first length of suture 912 in place in the illustrated suture loop configuration. A portion of a further length of suture material 918 is disposed within the bore 910 and engages with the first length of suture 912 as shown. As will be understood by one of ordinary skill in the art, an interface between the surfaces of the first 912 and second 918 lengths of suture material will exhibit desirably low friction. Further, the illustrated arrangement serves to couple the length of suture 918 effectively in relation to the anchor 900.

Figure 10:
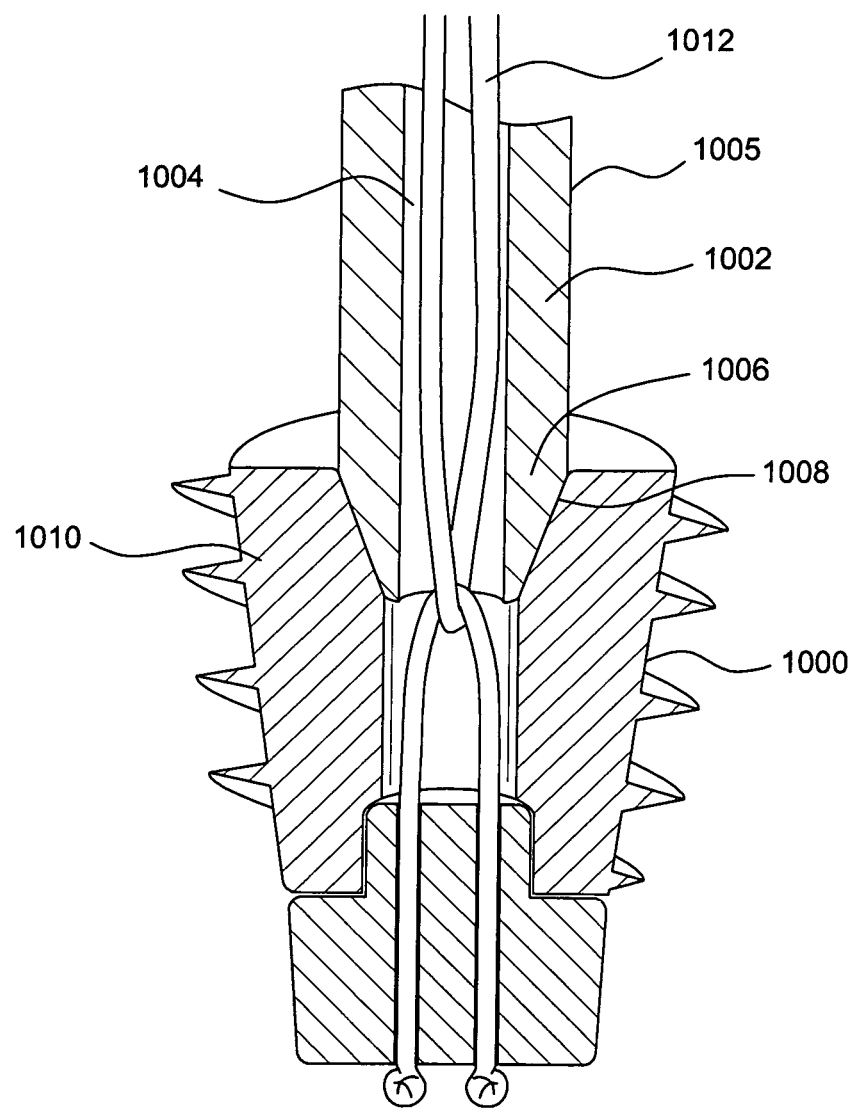
FIG. 10 shows, in cross-section, a portion of an anchor device and an insertion tool according to one embodiment of the invention.

FIG. 10 shows, in cross-section, a portion of a combination of an anchor 1000 with an insertion tool 1002. In the illustrated embodiment, the insertion tool 1002 includes a shaft portion 1005 having a longitudinal internal bore 1004 (i.e., a cannulated shaft). As shown, a distal portion 1006 of the shaft portion 1005 is adapted to engage with a tool engagement region 1008 of a fixing portion 1010 of anchor 1000. As a consequence of this arrangement, the fixing portion 1010 is adapted to receive a force such as a torque, transmitted by the shaft portion 1005.

As shown, the longitudinal bore 1004 of the shaft portion 1005 is adapted to receive a length of suture 1012 therewithin. This arrangement allows the shaft portion 1005 to engage with the tool engagement region 1008 without interference from the length of suture 1012. In certain embodiments of the invention, a kit is provided including an anchor having a stopper portion with a suture loop and a further length of suture, a fixing portion, and an insertion tool, all packaged together as a preassembled unit.

It should be noted that the various anchors illustrated and discussed above exhibit a variety of surface features including helical thread features and circular barb features and interrupted helical and circular barb features. In various embodiments of the invention particular features are selected for engagement with a particular substrate. Thus in one embodiment of the invention, an anchor is provided with a surface feature adapted to engage advantageously with cortical bone tissue.

In another embodiment, an anchor is provided with a surface feature adapted to engage with cancellous bone tissue. In certain other embodiments of the invention, a single anchor device may include surface features adapted to engage different substrates. Thus in one embodiment, an anchor is provided having a first surface feature adapted to engage cortical bone and a second surface feature adapted to engage cancellous bone tissue.

According to a further embodiment of the invention, it is advantageous to provide a stopper portion adapted to be substantially fixedly coupled to a corresponding fixing portion of a bone anchor. Such a fixing coupling can be advantageous both in terms of keeping the stopper portion and the fixing portion together during insertion of a bone anchor and also in terms of providing a robust coupling between the anchor and surrounding substrate, such as bone tissue.

Figure 11:
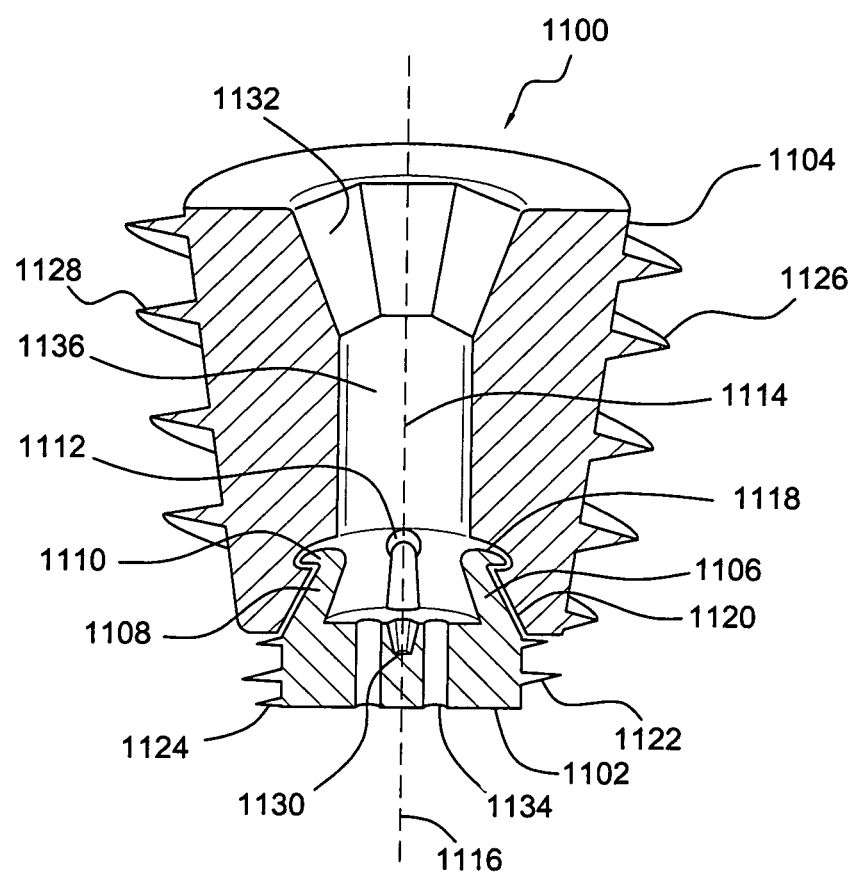
FIG. 11 shows, in cross-section, a portion of an anchor device including a stopper portion, a fixing portion and a detent mechanism, according to one embodiment of the invention.

FIG. 11 shows, in cross-section, a further embodiment of an anchor 1100. Anchor 1100 includes a first stopper portion 1102 and a second fixing portion 1104. Advantageously, the anchor 1100 includes a detent device 1106 adapted to substantially fixedly couple stopper portion 1102 to fixing portion 1104. In the embodiment illustrated as anchor 1100 the detent device 1106 includes a plurality of quasi-elastic arms (e.g., 1108) supporting a respective plurality of barbed hooks (e.g. 1110) or barbs. The arms 1108 are, in certain embodiments, coupled to or integral with stopper portion 1102. Each hook 1110 is adapted to be received within a corresponding cavity (e.g., 1112). Cavity 1112 opens into bore 1114 within fixing portion 1104.

Following a method according to one embodiment of the invention, stopper portion 1102 and fixing portion 1104 are aligned substantially coaxially along a longitudinal axis 1116. Forces are applied that urge stopper portion 1102 and fixing portion 1104 to move into proximity, each relative to the other. As this motion proceeds, proximal surface regions 1118 of barbs 1110 interfere mechanically with oblique surface regions 1120 of the fixing portion 1104. This mechanical interference motivates a pivotal deflection of the arms 1108 with respect to stopper portion 1102, moving the barbs 1110 progressively towards longitudinal axis 1116. This trend proceeds until the barbs 1110 reach the cavities 1112, whereupon elastic forces exerted by the arms move the barbs 1110 into the cavities 1112. Thereafter, the same elastic forces tend to retain barbs 1110 within cavities 1112.

One of skill in the art will appreciate that this arrangement tends to retain the stopper portion 1102 and fixing portion 1104 in substantially fixed relation to one another. In particular, it should be noted that the illustrated arrangement inhibits both further linear motion along the longitudinal axis 1116 with respect to one another and rotary motion of the stopper portion and fixing portion around longitudinal axis 1116 with respect to one another.

According to one embodiment of the invention, the stopper portion 1102 and fixing portion 1104 are urged together coaxially during assembly of an anchor device. As in the case of embodiment 1100, however, assembly of the stopper portion 1102 to the fixing portion 1104 is advantageously performed in situ within substrate tissue.

Accordingly, in one aspect of the invention, the illustrated stopper portion 1102 includes a first externally threaded surface feature 1122 including a substantially helical surface ridge 1124. It should be noted that first externally threaded surface feature 1122 is configured as a left-handed thread. The fixing portion 1104 includes a second externally threaded surface feature 1126 including a substantially helical surface ridge 1128. It should be noted that second externally threaded surface feature 1126 is configured as a right-handed thread. One of skill in the art will appreciate that the handedness identified above is merely exemplary and is readily reversed in alternative embodiments of the invention so that the stopper portion includes a right-handed thread and the fixing portion includes a left-handed thread.

According to one embodiment, the invention includes a method of inserting a first anchor portion by a left-handed rotation of the stopper portion so as to screwingly advance the stopper portion within a substrate; and thereafter inserting a fixing portion by a right-handed rotation of the fixing portion so as to screwingly advance the fixing portion within the substrate. According to one aspect of the invention as the fixing portion arrives in proximity to the stopper portion a substantially permanent coupling between the two anchor portions is made, whereupon the opposite threading of the two portions serves to substantially limit further rotation of either anchor portion of the combined anchor portion assembly.

In light of the here-described method it should be noted that, according to one embodiment, stopper portion 1102 includes a first receiving feature 1130 adapted to receive a first portion of a first insertion tool, and fixing portion 1104 includes a second receiving feature 1132 adapted to receive a second portion of a second insertion tool. It should be noted, however, that in certain embodiments, receiving portions can be configured so that a single insertion tool can be used in relation to both a stopper portion and a fixing portion. Although not shown, one of skill in the art will readily understand that a suture loop arrangement, as described above, can be disposed in relation to the illustrated bores 1134, 1136 of anchor 1100.

Figure 12:
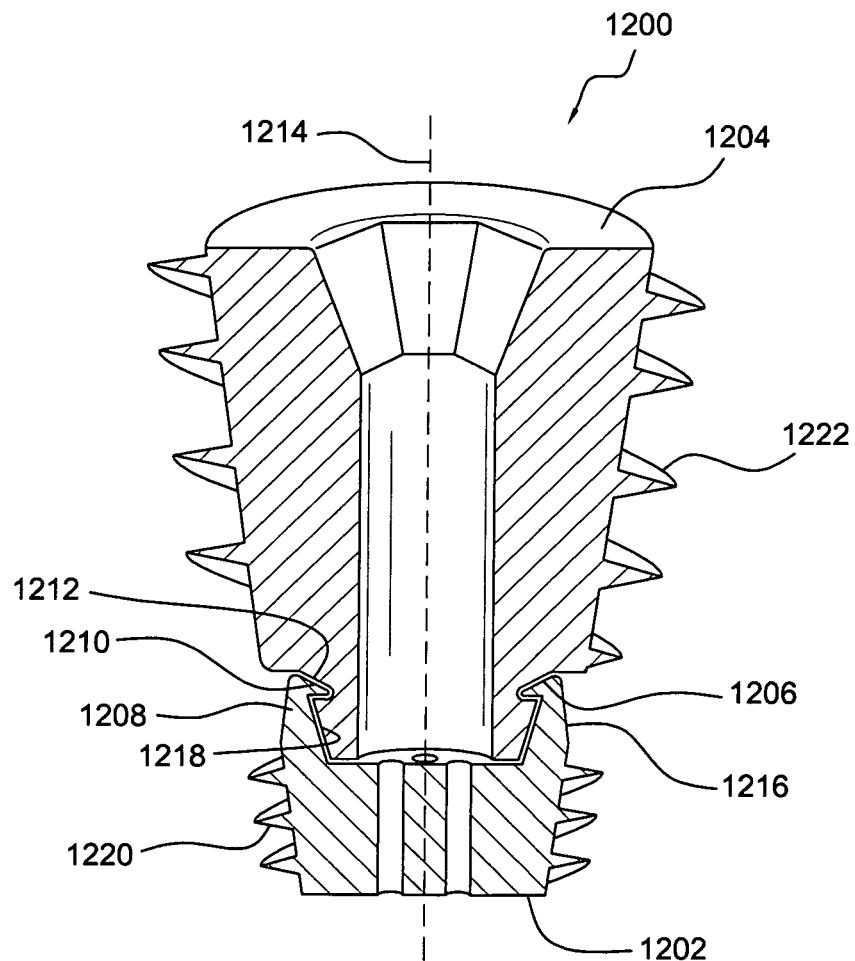
FIG. 12 shows, in cross-section, an anchor device according to a further embodiment of the invention.

FIG. 12 shows, in cross-section, a portion of a further embodiment of an anchor 1200 including a stopper portion 1202 and a fixing portion 1204. The anchor 1200 includes a detent device 1206. In the illustrated embodiment, detent device 1206 includes at least one reasonably flexible arm 1208 having a barbed hook portion 1210. The barbed hook 1210 is adapted to be received within a corresponding cavity 1212 of fixing portion 1204. It should be noted that, during an assembly process, reasonably flexible arm 1208 is adapted to be deflected outwardly away from longitudinal axis 1214 by interference between a first surface region 1216 of barbed hook portion 1210 and a corresponding external surface region 1218 of fixing portion 1204.

One of skill in the art will observe that whereas arm 1108 of anchor 1100 is deflected during assembly inwardly towards longitudinal axis 1116 and then relaxes hook 1110 outwardly into an internal cavity 1112 of fixing portion 1104, arm 1208 of anchor 1200 is deflected during assembly outwardly away from longitudinal axis 1214 and then relaxes inwardly into an external cavity 1212 of fixing portion 1204. In both illustrated embodiments 1100 and 1200, interfering surfaces 1120 and 1218 exhibit substantially circular symmetry about respective longitudinal axis 1116,1214 and are disposed generally obliquely with respect to the respective longitudinal axes. It should be noted that, in various embodiments, these interfering surfaces may exhibit simple and/or compound curvature.

As with the embodiment of anchor 1100, anchor 1200 includes opposing left-handed threads 1220 and right-handed threads 1222 so that once the stopper portion 1202 and fixing portion 1204 are assembled in situ within a substrate, and detent portion 1206 is activated to lock the two portions together, the opposing threads tend to prevent further rotation and other motion of the completed assembly.

It should be noted that, in certain embodiments, a first, relatively narrow, receiving hole is bored in a substrate to receive the stopper portion. In some embodiments, this receiving hole is in advance of insertion of the stopper portion. In other embodiments, the stopper portion includes a self-tapping thread. In still other embodiments, the stopper portion includes a self-punching self-tapping thread adapted to allow insertion of the stopper portion without the predrilling of a receiving hole. In certain embodiments no receiving hole is predrilled, but a lead hole of substantially smaller diameter than the stopper portion is predrilled in the substrate.

In other embodiments, a receiving hole is drilled that includes a relatively narrow diameter portion adapted to receive the stopper portion and a relatively wider diameter portion adapted to receive the fixing portion of the anchor. According to certain methods of the invention, a plural-diameter hole is prepared in a single operation using an appropriate tool of stepped diameter. Likewise, an appropriate tool may be used to simultaneously drill and tap a receiving hole of a single or of a plural diameter.

Figure 13:
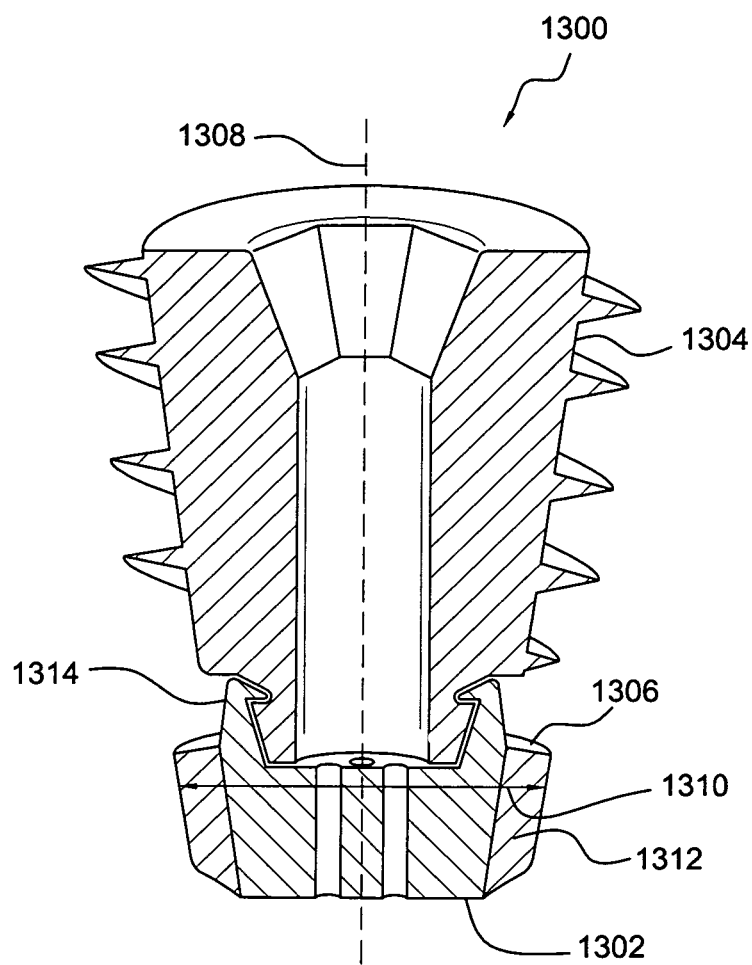
FIG. 13 shows, in cross-section, an anchor device according to another embodiment of the invention.

FIG. 13 shows an anchor 1300 including a stopper portion 1302 and a fixing portion 1304. The stopper portion 1302 includes one or more substantially radially projecting vanes 1306. The vanes 1306 are adapted to prevent rotation of stopper portion 1302 about a longitudinal axis 1308 when the stopper portion 1302 is disposed within a substrate matrix such as, for example, osseous tissue.

According to one method within the scope of the invention, an appropriately sized receiving hole is prepared in a region of substrate bone tissue. The receiving hole is configured to have a diameter appropriately less than a corresponding diameter 1310 across the vanes 1306 of stopper portion 1302. Stopper portion 1302 is disposed coaxially at a mouth of the receiving hole and urged along longitudinal axis 1308 into the receiving hole. According to one embodiment of the invention, vanes 1306 are adapted to cut into, or otherwise displace, a portion of the substrate bone disposed radially with respect to the receiving hole as the stopper portion 1302 is advanced into the receiving hole. Consequently, when the stopper portion 1302 has been sufficiently received into the receiving hole its rotation about longitudinal axis 1308 is substantially inhibited by a mechanical interference between external surfaces (e.g. 1312) of the vanes and the surrounding substrate.

Thereafter, fixing portion 1304 is advanced with rotation into the receiving hole until a detent mechanism 1314 engages. Thereafter, the mechanical engagement between the stopper portion 1302 and the fixing portion 1304, in combination with the action of the vanes 1306 to inhibit rotation of the stopper portion 1302 serves to substantially prevent undesirable counter-rotation and consequent withdrawal of the fixing portion 1304.

Figure 14:
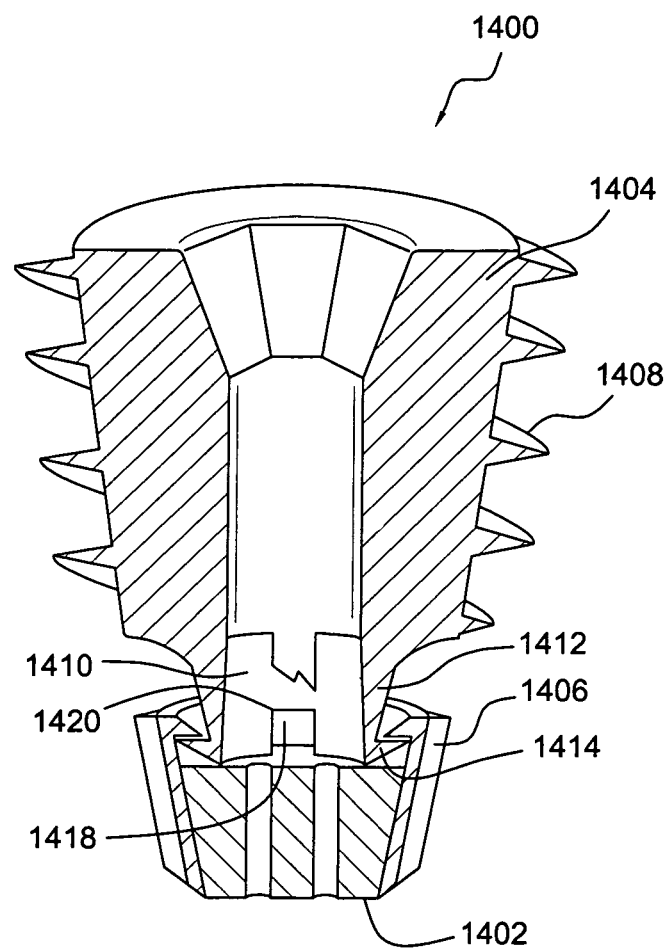
FIG. 14 shows, in cross-section, an anchor device according to still another embodiment of the invention.

FIG. 14 shows a further embodiment of an anchor 1400 according to principles of the invention. The anchor 1400 includes a stopper portion 1402 and a fixing portion 1404. The stopper portion 1402 has at least one anti-rotation vane 1406. The fixing portion 1404 has an external surface thread feature 1408. A detent mechanism 1410 includes a plurality of substantially flexible arms 1412 that are integral with or coupled to fixing portion 1404. The arms 1412 include respective barbed hooks 1414 adapted to be received internally within stopper portion 1402.

Figure 15:
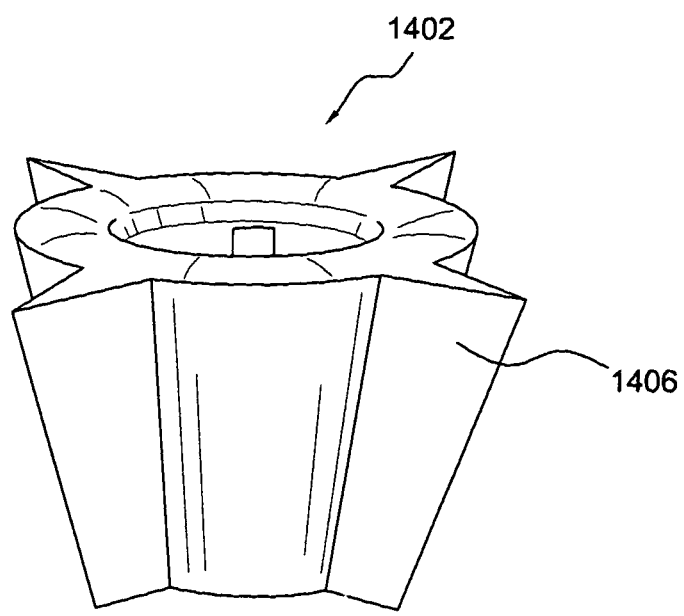
FIG. 15 shows, in perspective view, a stopper having an anti-rotation vane according to one embodiment of the invention.

FIG. 15 shows a further perspective view of stopper 1402 including four illustrative vanes 1406.

Figure 16:
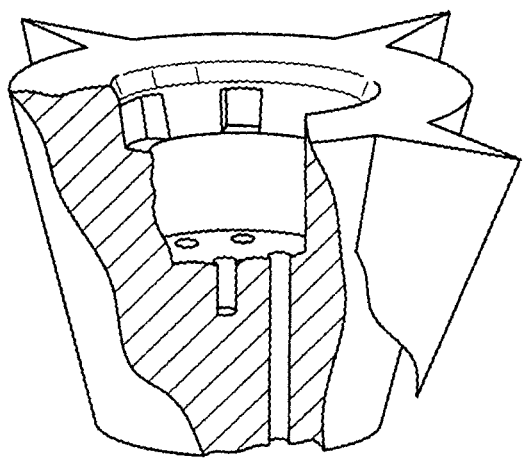
FIG. 16 shows, in cutaway perspective view, a stopper according to one embodiment of the invention.

FIG. 16 shows a further cutaway view of stopper 1402. In the illustrated embodiment, stopper portion 1402 includes a plurality of receiving cavities 1418 adapted to receive and retain the barbed hooks 1414. The illustrated receiving cavities have a substantially rectangular circumferential profile 1420, however alternative profiles including, without limitation, circular, triangular, polygonal and curved are contemplated. In addition, it is anticipated that the number of receiving cavities 1418 may differ from a number of barbed hooks 1414. For example, there may be more receiving cavities than barbed hooks or more barbed hooks than receiving cavities.

Figure 17:
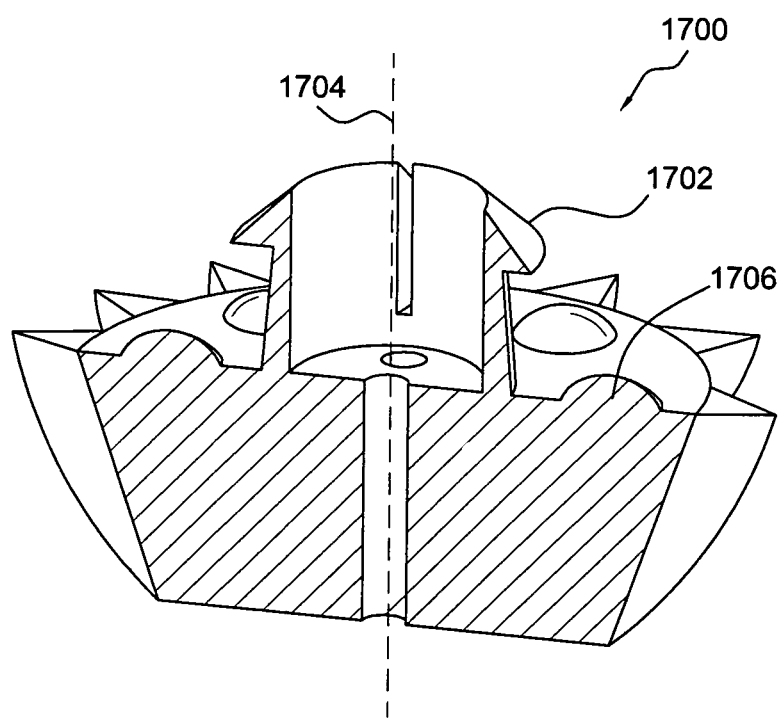
FIG. 17 shows, in quasi-cross-sectional view, a stopper including a detent mechanism according to one embodiment of the invention.

It should be understood that the above-described barbed hooks are merely exemplary of a wide variety of other detent mechanisms that are contemplated within the scope of the invention. Thus, FIG. 17 shows a stopper 1700 according to a further embodiment of the invention including a first barbed-hook detent feature 1702 adapted to prevent linear withdrawal of a fixing portion (not shown) along longitudinal axis 1704 with respect to stopper 1700. A separate hemispherical detent feature 1706 is adapted to be received within a corresponding cavity of the fixing portion to inhibit rotation about longitudinal axis 1704 of the fixing portion with respect to the stopper portion 1700.

Figure 18:
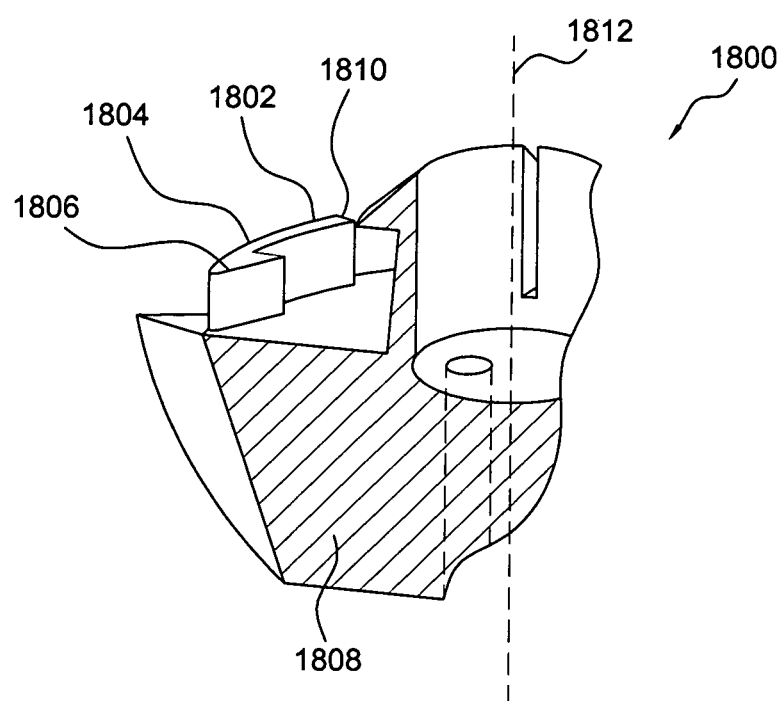
FIG. 18 shows, in cutaway perspective view, a stopper including a detent mechanism according to another embodiment of the invention.

It will be appreciated that, while detent feature 1706 is shown as a substantially hemispherical projection, well adapted to be received in a corresponding substantially concave hemispherical recess of a fixing portion, alternative arrangements are possible. For example a concave recess may be provided on the stopper portion while a corresponding convex projection may be provided on the fixing portion. Likewise, each of the stopper portion and the fixing portion may include both convex and concave features. Further, the hemispherical shape of the projection is merely illustrative of a wide variety of possible shapes and configurations that fall within the scope of the invention in its various embodiments. Thus, for example, FIG. 18 shows a portion of a stopper 1800 including an anti-rotation detent feature 1802 having a generally flexible arm 1804 and a barbed hook 1806 at one end thereof.

The generally flexible arm 1804 is integral with or coupled to a body 1808 of the stopper portion 1800 at an end 1810 opposite to the barbed hook 1806. In the illustrated embodiment, the arm 1804 is adapted to deflect, so as to allow the barbed hook 1806 to be displaced generally radially outward with respect to longitudinal axis 1812. Thereafter, the arm 1804 is adapted to resile so as to position a portion of the barbed hook 1806 within a corresponding cavity of a fixing portion (not shown). Consequently, as will be understood by one of skill in the art, the fixing portion and stopper portion 1800 are adapted to be locked in substantially fixed spatial relation to one another and to a surrounding substrate.

Figure 19:
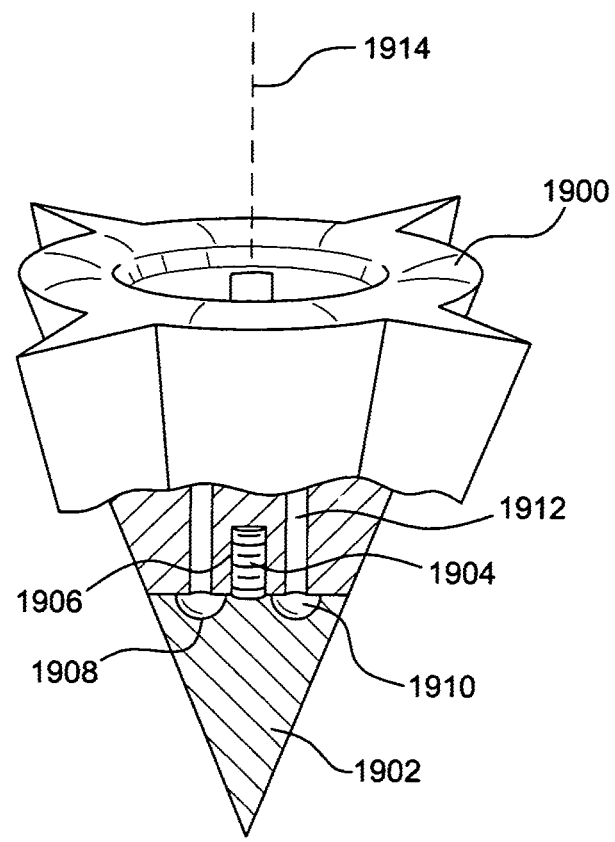
FIG. 19 shows, in cutaway perspective view, a stopper including a piercing point according to one embodiment of the invention.

FIG. 19 shows, in cutaway cross-sectional view, a stopper portion 1900 according to a further embodiment of the invention. The stopper portion 1900 is adapted to be coupled to an exemplary piercing point 1902. In the illustrated embodiment, the piercing point includes a fastener, shown here for example as an externally threaded stud 1904, adapted to be received within an internally threaded bore 1906 of the stopper 1900. In the illustrated embodiment, the piercing point includes an annular cavity or channel 1908 adapted to accommodate a knot 1910 of a suture loop (not shown).

While the piercing point 1902 is shown here as a discrete component adapted to be assembled to stopper portion 1900, one of skill in the art will appreciate that stopper 1900 could equally well be prepared to include an integral piercing point. In the case of a stopper having an integral piercing point, suture channels (e.g., 1912) can be configured to exit the stopper longitudinally and/or radially with respect to a longitudinal axis 1914 of the stopper 1900. It should also be understood that the stopper and piercing point can be made of the same or differing materials according to the requirements of a particular embodiment and application.

Thus, in one embodiment a fixing portion, a stopper portion, and a piercing point may each be made of any one of a biocompatible material including natural and synthetic polymers such as, for example, poly-ether-ether-ketone (PEEK); reinforced polymer materials including reinforcing sheets and/or particles and/or fibers of, for example, one or more of, carbon fibers, carbon nano-materials, glass fibers and metallic fibers; precious metals, stainless steel, titanium and other metals; porcelain, alumina and other ceramics including, for example, aluminum oxide, calcium oxide, calcium phosphate hydroxyapatite, and zirconium, and combinations thereof.

Figure 20:
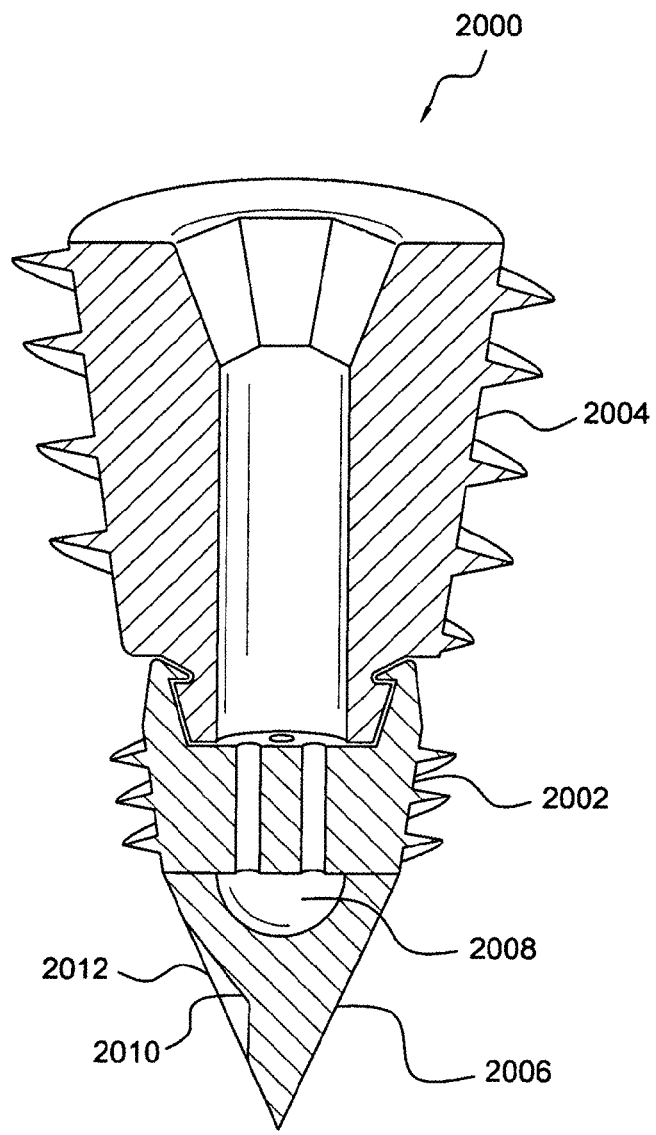
FIG. 20 shows, in cross-section, an anchor according to one embodiment of the invention.

FIG. 20 shows an anchor 2000 according to a further embodiment of the invention. Anchor 2000 includes a first stopper portion 2002 and a second fixing portion 2004. The stopper portion 2002 includes a piercing point 2006. According to one embodiment of the invention, piercing point 2006 includes a cavity 2008, here shown as a generally hemispherical cavity adapted to receive a suture knot therewithin. The exemplary piercing point illustrated here also has a depressed region 2010 and a cutting edge 2012 adapted to facilitate a substrate piercing function of the piercing point 2006.

Figure 21:
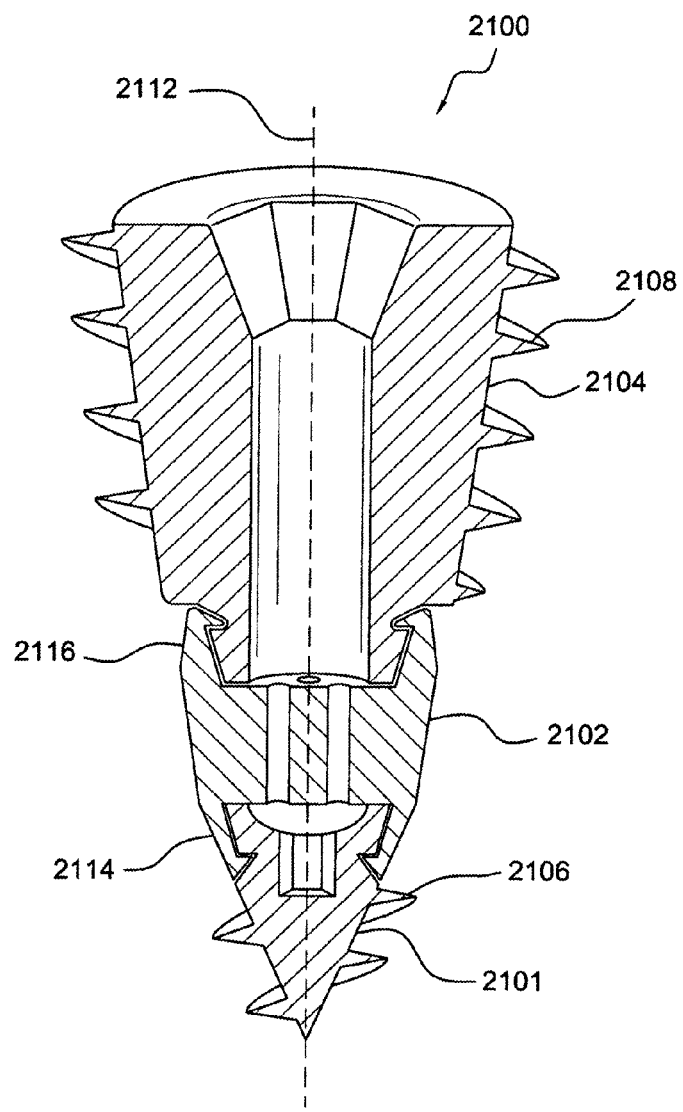
FIG. 21 shows, in cross-section, an anchor according to another embodiment of the invention.

FIG. 21 shows, in cross section, an anchor 2100 according to a further embodiment of the invention. Anchor 2100 includes a first piercing point 2101, a second stopper portion 2102, and a third fixing portion 2104. As shown, the piercing point 2101 includes a first surface feature, here shown as left-handed threads 2106. The fixing portion 2104 includes a second surface feature, here shown as right-handed threads 2108. In the presently illustrated embodiment, the stopper portion 2102 does not include a surface feature adapted to prevent rotation or withdrawal along longitudinal axis 2112 of the stopper portion 2102. The stopper portion 2102 does include, however, detent devices 2114, 2116, adapted to substantially fixedly couple the stopper portion 2102 to the piercing point 2101 and the fixing portion 2104 respectively.

It should be appreciated that in other embodiments, the stopper portion includes an anti-rotation or anti-extraction surface feature such as a plurality of vanes. In other embodiments, one or more of the piercing point 2101 and the fixing portion 2104 includes an alternative anti-rotation or anti-extraction surface feature such as, for example, a plurality of vanes.

Figure 22:
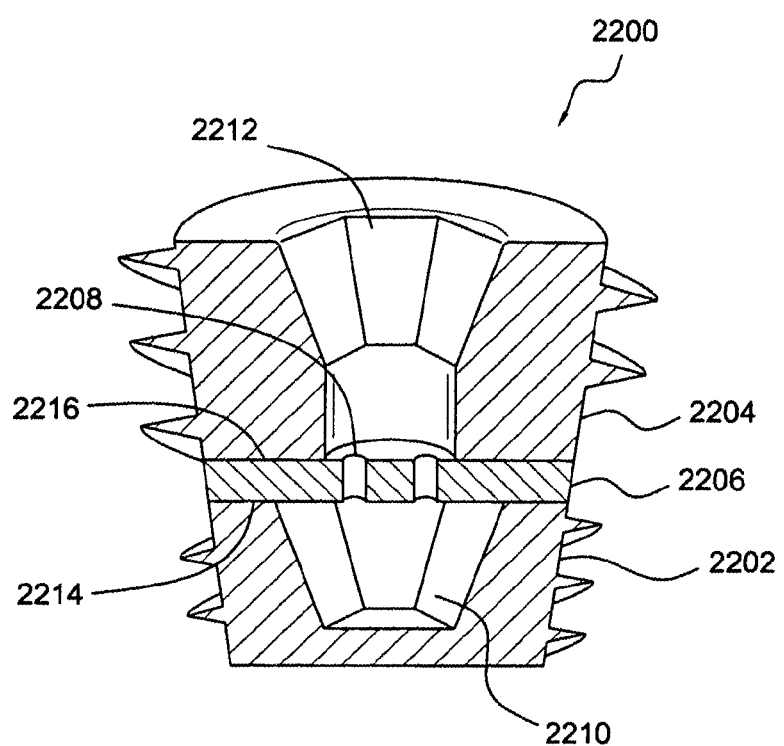
FIG. 22 shows, in cross-section, an anchor according to still another embodiment of the invention.

FIG. 22 shows, in cross section, a further anchor 2200. Anchor 2200 includes a first stopper portion 2202, a second fixing portion 2204, and a retainer portion 2206. The retainer portion 2206 includes at least one longitudinal bore 2208 adapted to receive a portion of a suture therewithin. As illustrated, the stopper portion 2202 includes a surface feature, here shown as left-handed threads, for example. The fixing portion 2204 includes a surface feature, here shown as right-handed threads, for example. Both the stopper portion 2202 and in the fixing portion 2204 include respective tool receiving features 2210, 2212. In one embodiment, the retainer portion 2206 includes a contact surface 2214 adapted to engage a corresponding surface of stopper portion 2202.

In the illustrated embodiment, the retainer portion 2206 also includes a contact surface 2216 adapted to engage a corresponding surface of fixing portion 2204. According to one embodiment of the invention, contact surfaces 2214 and 2216 are adapted to frictionally engage corresponding surfaces of the stopper portion 2202 and fixing portion 2204. In other embodiments, the anchor 2200 is adapted to receive, for example, a chemical adhesive material, at surfaces 2214 and 2216. In still other embodiments, the anchor 2200 is adapted to be treated after insertion into a substrate to form a physical bond at surfaces 2214 and 2216. For example, one or more of a thermal weld and an ultrasonic weld may be formed at surfaces 2214 and 2216 to prevent decoupling of the stopper portion 2202 from the fixing portion 2204 and the retainer portion 2206.

Figure 23:
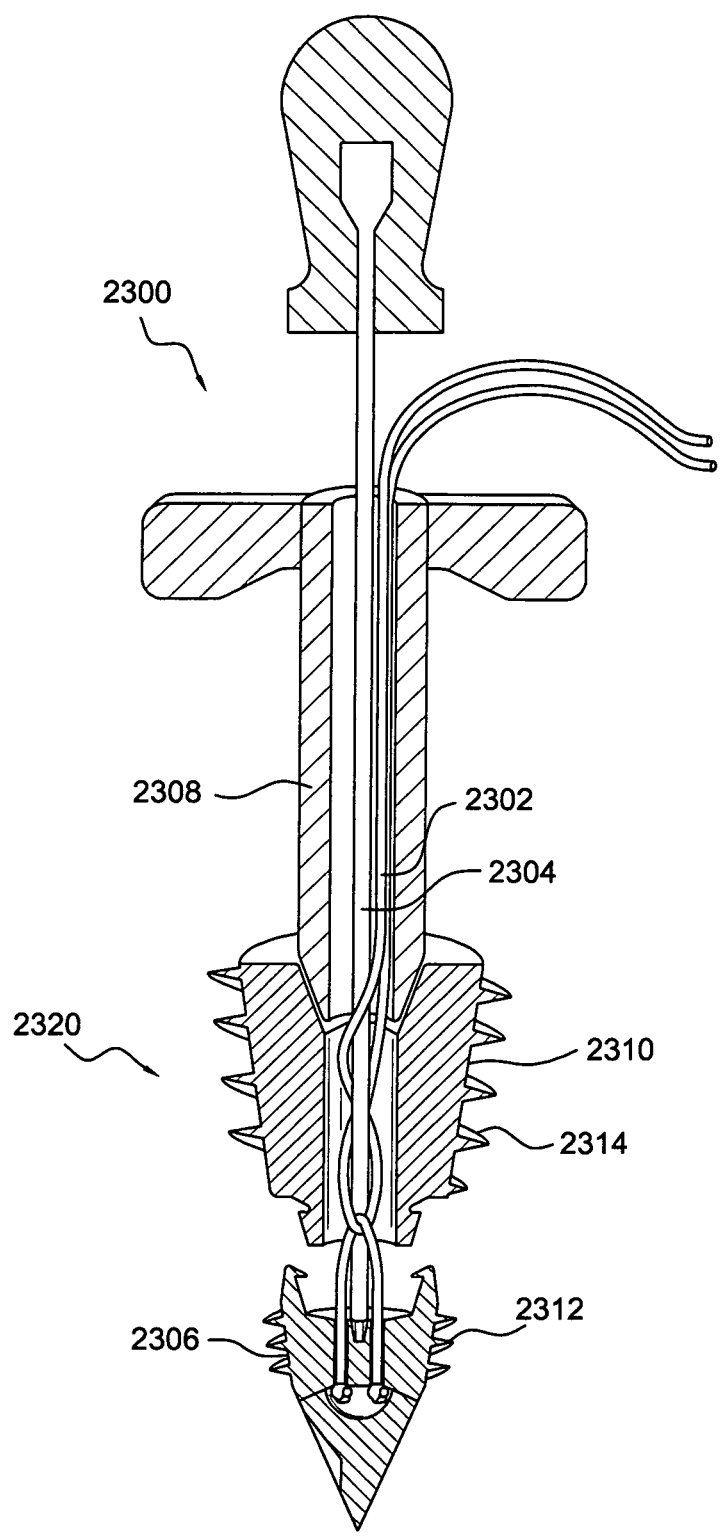
FIG. 23 shows in cross-section, a portion of an anchor and insertion tool kit according to one embodiment of the invention.

One of skill in the art will appreciate that a variety of methods are evident from the above-provided description and included within the scope of the present invention as disclosed. Thus, according to one method of the invention, a first hole is drilled or pierced into a substrate such as a bone. A cannulated insertion tool 2300, as shown in FIG. 23 has a suture 2302 disposed generally longitudinally adjacent to a first substantially solid shaft 2304 thereof. The first shaft 2304 is used to drive a self-tapping stopper portion 2306 into the hole by a leftward rotation of the first shaft 2304. Subsequently, a further portion of the cannulated insertion tool, including a second cannulated shaft 2308 coaxially encircling the first substantially solid shaft 2304 is used to drive a self-tapping fixing portion 2310 into the hole by a rightward rotation of the second shaft 2308 until the stopper portion 2306 and the fixing portion 2310 engage and lock together. Thereafter the opposing sense of the threads 2312, 2314 of the stopper portion and of the fixing portion respectively prevent subsequent rotation and withdrawal of the resulting anchor assembly 2320.

Figure 24:
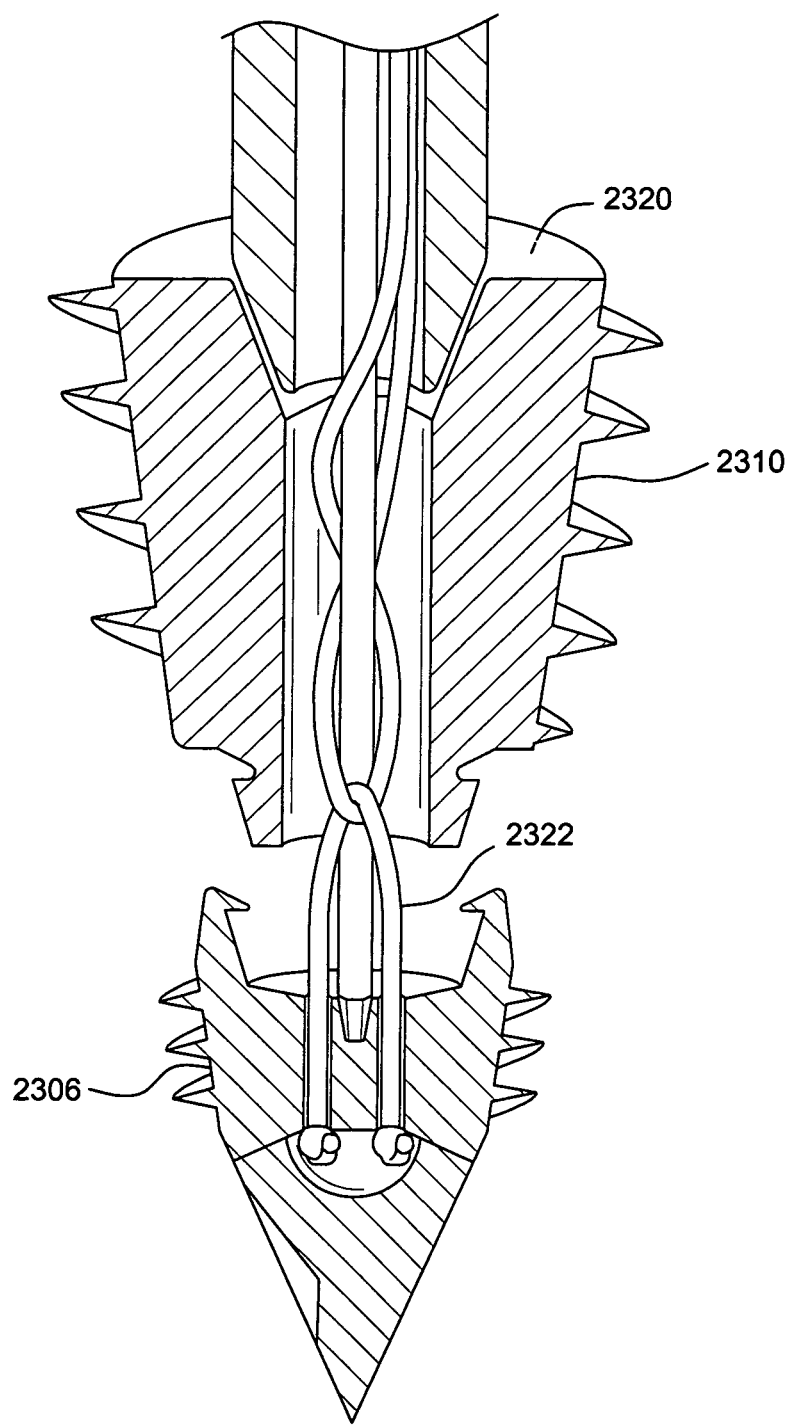
FIG. 24 shows, in cross-section, a portion of an anchor and insertion tool kit as used in a method according to one embodiment of the invention.

FIG. 24 shows the relationship of the stopper portion 2306, including suture loop 2322 and fixing portion 2310 in additional detail. In a typical application, the fixing portion 2310 will be installed in a substrate bone so that proximal surface 2320 is ultimately disposed substantially flush with an external surface of the bone. In another embodiment of the invention, surface 2320 is ultimately disposed a short distance inwardly of the external surface of the bone. For example surface 2320 may be disposed between about 0 mm and at least about 0.5 mm below the external surface of the substrate bone. It should be further noted that in certain cases, elements of the anchor are tapped, pounded and/or pressed into place, rather than rotated into place.

One of skill in the art will appreciate that a threaded suture anchor can be deployed into cortical bone. Purchase in cortical bone is enhanced by a narrow (e.g., approximately 1.5 mm) thread pitch. A wider thread pitch (e.g., approximately 3 mm) is advantageously deployed in cancellous bone. The push-in anchor has very broad application in areas such as the foot, the hand, and the shoulder. Advantageously, the push-in anchor has a compact size. This compact size is advantageous and allows for greater maneuverability in tight articular spaces.

While the exemplary embodiments described above have been chosen primarily from the field of soft tissue to bone reattachment, one of skill in the art will appreciate that the principles of the invention are equally well applied, and that the benefits of the present invention are equally well realized, in a wide variety of other applications, for example, the relative repositioning of multiple bone pieces and prosthetic devices. Further, while the invention has been described in detail in connection with the presently preferred embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Accordingly, the invention is not to be seen as limited by the foregoing description, but is only limited by the scope of the appended claims.

The invention claimed is:

1. An anchor comprising:
   a stopper portion, said stopper portion including a first body, said first body including a first bone-interface surface having a first circumferential thread oriented in a first sense, said first body having first and second through-holes therein, said first and second through-holes being disposed in generally parallel spaced relation to one another and substantially parallel to a longitudinal axis of said anchor;
   a fixing portion, said fixing portion including a second body, said second body including a second bone-interface surface having a second circumferential thread oriented in a second sense opposite said first sense, said second bone interface surface being adapted to interfere with a corresponding region of a patient's bone so as to prevent a premature displacement of said fixing portion from an installed location with respect to said bone, said second body having at least a third through-hole, said third through hole being disposed generally parallel to said longitudinal axis of said anchor; and
   a locking device, said locking device including a first feature of said first body and a second feature of said second body, said first and second features being adapted to present respective interfering surfaces to one another so as to limit a rotation of said stopper portion with respect to said fixing portion about said longitudinal axis of said anchor.

2. An anchor as defined in claim 1 wherein said first and second features comprise a projection and a recess respectively, said projection and recess including said interfering surfaces respectively, wherein said interfering surfaces each includes a generally planar surface region.

3. An anchor as defined in claim 2 wherein said projection comprises a barb feature.

4. An anchor as defined in claim 2 wherein said projection is supported on a generally elastic member, said generally elastic member being arranged and adapted to urge said projection into said recess during use of said anchor.

5. An anchor as defined in claim 4 wherein said generally elastic member exhibits a longitudinal axis, said longitudinal axis being disposed in a plane substantially normal to a longitudinal axis of said anchor.

6. An anchor as defined in claim 4 wherein said generally elastic member exhibits a longitudinal axis, said longitudinal axis being disposed in a plane substantially parallel to a longitudinal axis of said anchor.

7. An anchor as defined in claim 1 wherein said first feature comprises a generally ellipsoid projection.

8. An anchor as defined in claim 7 wherein said generally ellipsoid projection comprises a generally hemispherical projection.

* * * * *